United States Patent [19]
Yamamoto et al.

[11] 3,989,829
[45] Nov. 2, 1976

[54] 1,4-BENZODIAZEPINES

[75] Inventors: Hisao Yamamoto, Kobe; Shigeho Inaba, Takarazuka; Toshiyuki Hirohashi, Ibaragi; Michihiro Yamamoto, Nishinomiya; Kikuo Ishizumi, Toyonaka; Mitsuhiro Akatsu, Saitama; Isamu Maruyama, Minoo; Yoshiharu Kume, Takarazuka; Kazuo Mori, Kobe; Takahiro Izumi, Takarazuka, all of Japan

[73] Assignee: Sumitomo Chemical Company, Limited, Osaka, Japan

[22] Filed: July 10, 1975

[21] Appl. No.: 594,771

Related U.S. Application Data

[63] Continuation-in-part of Ser. No. 301,952, Oct. 30, 1972, abandoned, which is a continuation of Ser. No. 26,409, April 7, 1970, Pat. No. 3,778,433.

[30] Foreign Application Priority Data

Apr. 18, 1969  Japan.............................. 44-30601
Apr. 18, 1969  Japan.............................. 44-30603
Apr. 18, 1969  Japan.............................. 44-30606
Apr. 24, 1969  Japan.............................. 44-32220
May 28, 1969   Japan.............................. 44-41873
May 29, 1969   Japan.............................. 44-42213
July 3, 1969   Japan.............................. 44-52868

[52] U.S. Cl. .......................... 424/244; 260/239.3 D
[51] Int. Cl.² ..................................... C07D 243/24
[58] Field of Search............... 260/239.3 D; 424/244

[56] References Cited
UNITED STATES PATENTS 3,391,138  7/1968  Archer et al................. 260/239.3 D
3,819,602  6/1974  Fryer et al................... 260/239.3 D

OTHER PUBLICATIONS

Sternbach et al. "Some Aspects of Structure–Activity Relationship in Psychotropic Agents of the 1,4-Benzodiazepine Series" A Symposium Held at the Regional Research Laboratory, Hyderbad, India CSIR, New Delhi, India (1966).

Primary Examiner—Henry R. Jiles
Assistant Examiner—Robert T. Bond
Attorney, Agent, or Firm—Stevens, Davis, Miller & Mosher

[57] ABSTRACT

Benzodiazepine derivatives of the formula,

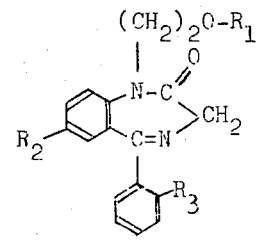

wherein $R_1$ is a $C_{2-4}$ alkenyl group, $R_2$ is a halogen atom and $R_3$ is a hydrogen or halogen atom, which are useful as minor tranquilizer and anticonvulsant. These compounds are prepared by reacting a compound of the formula,

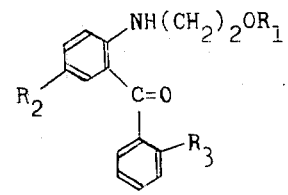

wherein $R_1$, $R_2$, and $R_3$ are as defined above, with a compound of the formula,

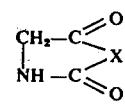

wherein X is an oxygen or sulfur atom.

8 Claims, No Drawings

1,4-BENZODIAZEPINES

CROSS REFERENCE

The present application is a continuation-in-part application of U.S. Ser. No. 301,952 filed on Oct. 30, 1972, now abandoned which is in turn a continuation application of Ser. No. 26,409 filed on Apr. 7, 1970, now U.S. Pat. No. 3,778,433.

The present invention relates to novel 1,4-benzodiazepine derivatives, pharmaceutically acceptable salts thereof, and pharmaceutical compositions comprising them.

More particularly, the present invention provides novel 1,4-benzodiazepine derivatives represented by the formula,

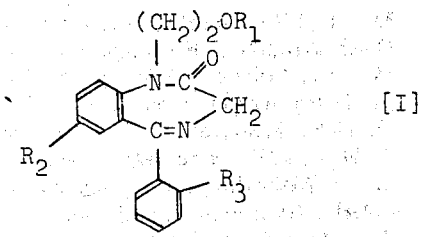

[I]

wherein $R_1$ is a $C_{2-4}$ alkenyl group, $R_2$ is a halogen atom and $R_3$ is a hydrogen or halogen atom, or pharmaceutically acceptable salts thereof, and pharmaceutical compositions comprising such derivatives and pharmaceutically acceptable carriers. The 1,4-benzodiazepine derivatives [I] as defined above show minor tranquilizing, muscle relaxant and anticonvulsant activities, and they are useful as minor tranquilizer, muscle relaxant and anticonvulsant. Particularly the 1,4-benzodiazepine derivatives [I] have characteristically potent minor tranquilizing activity. Further, the superiority of the present invention is that the 1,4-benzodiazepine derivatives [I] can be administered for long period since they have no tolerance.

The preferable class of the 1,4-benzodiazepine derivatives [I] is a compound of the formula,

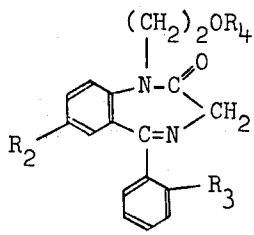

wherein $R_2$ and $R_3$ are as defined above and $R_4$ is a $C_{2-3}$ alkenyl group.

Accordingly, a basic object of the present invention is to provide novel 1,4-benzodiazepine derivatives [I] and their pharmaceutically acceptable salts which have excellent pharmacological properties. Another object of this invention is to provide pharmaceutical compositions comprising such novel and useful 1,4-benzodiazepine derivatives or their salts, and pharmaceutically acceptable carriers.

These and other objects of the invention will be apparent from the following descriptions.

According to the present invention, the 1,4-benzodiazepine derivatives [I] are prepared by reacting a compound of the formula,

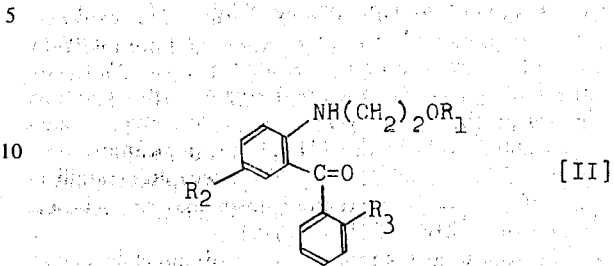

[II]

wherein $R_1$, $R_2$, and $R_3$ are as defined above, with a compound of the formula,

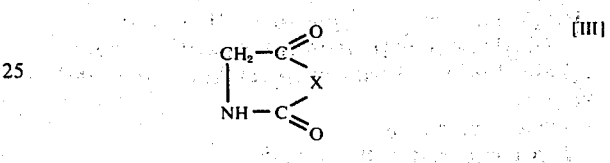

[III]

wherein X is an oxygen or sulfur atom.

The reaction may be carried out in the presence of an acid in an inert solvent (e.g. chloroform, carbon tetrachloride, methylene chloride, ethylene chloride, ether, diisopropyl ether, tetrahydrofuran, dioxane, water, methanol, ethanol, dimethylformamide, dimethyl sulfoxide) at a temperature from about room temperature to the boiling temperature of the solvent used. Suitable acids include hydrogen chloride, hydrogen bromide, sulfuric acid, phosphoric acid, polyphosphoric acids, boron trifluoride and p-toluenesulfonic acid.

Thus obtained 1,4-benzodiazepin derivatives [I] form pharmaceutically acceptable salts with a variety of inorganic and organic acids such as sulfuric, phosphoric, hydrochloric, hydrobromic, nitric, oxalic, malonic, succinic, lactic, tartaric, maleic, fumaric, formic, acetic and salicylic acids.

The 1,4-benzodiazepin derivatives [I] or salts thereof can be administered parenterally or orally in therapeutic dosage forms with dosage adjusted to individual needs, that is, in solid or liquid dosage forms such as tablets, dragees, capsules, suspensions, solutions, elixirs and the like.

A typical tablet may be constituted from 1 to 20 per cent by weight of a binder e.g. tragacanth), to 20 per cent by weight of a lubricant (e.g. talcum, magnesium stearate), an average dose of the active ingredient and q.s. 100 percent by weight of a filler (e.g. lactose). The usual oral dosage is 1 to 1000 mg per an adult person preferably 1 to 100 mg.

The present invention is illustrated more particularly by the following examples. However, it should be understood that the present invention is not limited to them.

EXAMPLE 1

To a solution of 0.3g of 2-(β-vinyloxyethyl)amino-5-chlorobenzophenone in 20 ml of dry methylene chloride is added 0.27g of oxazolidin-2,5-dione. To the mixture is added 20 ml of ethereal hydrogen chloride under cooling. The mixture is allowed to stand at room temperature with occasional stirring. The reaction mixture is poured into water, basified with aqueous ammonia and extracted with methylene chloride. The extracts are combined and dried over sodium sulfate, and the solvent is removed under reduced pressure. The residue is dissolved in ether and treated with ethanolic hydrogen chloride to give 1-(β-vinyloxyethyl)-5-phenyl-7-chloro-1,3-dihydro-2H-1,4-benzodiazepin-2-one hydrochloride, m.p. 213° – 215° C (dec.). Recrystallization from isopropanolchloroform gives colorless prisms, m.p. 216° – 218° C (dec.).

The following compounds were obtained in accordance with the manner similar to that of Example 1:

1-(β-Vinyloxyethyl)-5-(o-fluorophenyl)-7-chloro-1,3-dihydro-2H-1,4-benzodiazepin-2-one, m.p. 82° – 84° C.

1-(β-Vinyloxyethyl)-5-(o-chlorophenyl)-7-chloro-1,3-dihydro-2H-1,4-benzodiazepin-2-one, m.p. 118° – 119.5° C.

1-(β-Allyloxyethyl)-5-phenyl-7-chloro-1,3-dihydro-2H-1,4-benzodiazepin-2-one, m.p. 91° – 93° C.

1-(β-Allyloxyethyl)-5-(o-fluorophenyl)-7-chloro-1,3-dihydro-2H-1,4-benzodiazepin-2-one, m.p. 88° – 90° C.

What is claimed is:

1. A compound of the formula,

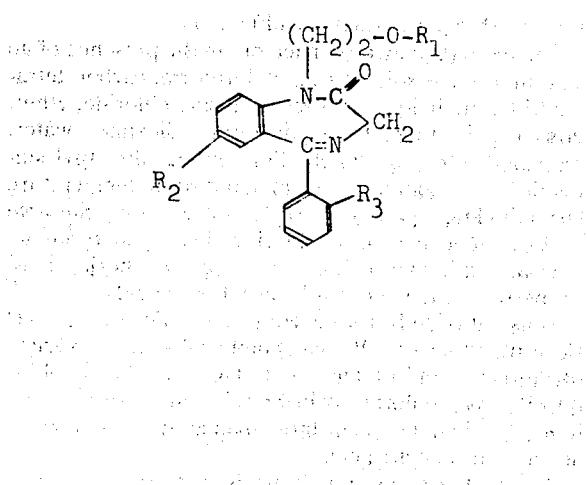

wherein $R_1$ is a $C_{2-4}$ alkenyl group, $R_2$ is a halogen atom and $R_3$ is a hydrogen or halogen atom, and its pharmaceutically acceptable salts.

2. A compound of the formula,

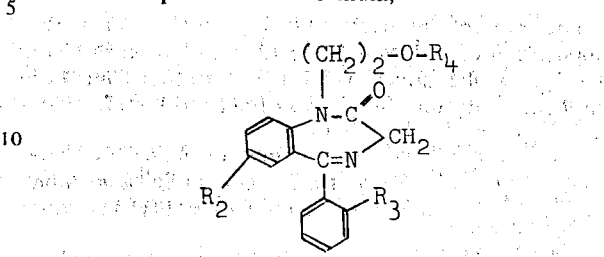

wherein $R_2$ and $R_3$ are as defined in claim 1 and $R_4$ is a $C_{2-3}$ alkenyl group, and its pharamaceutically acceptable salts.

3. 1-(β-Allyloxyethyl-5-(o-fluorophenyl)-7-chloro-1,3-dihydro-2H-1,4-benzodiazepin-2-one.

4. 1-(β-Allyloxyethyl)-5-phenyl-7-chloro-1,3-dihydro-2H-1,4-benzodiazepin-2-one.

5. 1-(β-Vinyloxyethyl)-5-(o-fluorophenyl)-7-chloro-1,3-dihydro-2H-1,4-benzodiazepine-2-one.

6. 1-(β-Vinyloxyethyl)-5-phenyl-7-chloro-1,3-dihydro-2H-1,4-benzodiazepin-2-one.

7. A tranquilizing and anti-convulsant composition comprising an effective amount of a compound of claim 1 together with a pharmaceutically acceptable carrier.

8. A method for tranquilizing and treatment of convulsions which comprises treating a patient with an effective amount of a compound of claim 1.

* * * * *